United States Patent [19]

Thomas et al.

[11] Patent Number: 6,049,024
[45] Date of Patent: Apr. 11, 2000

[54] COMPOSITE FABRIC FOR COVERSTOCK HAVING SEPARATE LIQUID PERVIOUS AND IMPERVIOUS REGIONS

[75] Inventors: Harold Edward Thomas, Greer; James O. Reeder, Greenville, both of S.C.

[73] Assignee: BBA Nonwovens Simpsonville, Inc., Simpsonville, S.C.

[21] Appl. No.: 09/082,773

[22] Filed: May 21, 1998

Related U.S. Application Data

[60] Provisional application No. 60/047,440, May 22, 1997.

[51] Int. Cl.$^7$ .................................................. A61F 13/15
[52] U.S. Cl. ...................... 604/367; 604/385.1; 604/365; 604/378
[58] Field of Search .................................. 604/378, 367, 604/365, 385.1; 428/98, 198, 196

[56] References Cited

U.S. PATENT DOCUMENTS

| | | |
|---|---|---|
| 4,230,113 | 10/1980 | Mehta . |
| 4,526,825 | 7/1985 | Whitehead . |
| 4,585,449 | 4/1986 | Karami . |
| 4,798,603 | 1/1989 | Meyer et al. . |
| 4,994,037 | 2/1991 | Bernardin . |
| 5,147,345 | 9/1992 | Young et al. . |
| 5,181,563 | 1/1993 | Amaral . |
| 5,300,053 | 4/1994 | Genaro . |
| 5,334,177 | 8/1994 | Cohen . |
| 5,364,381 | 11/1994 | Soga et al. . |
| 5,391,160 | 2/1995 | Runeman et al. . |
| 5,422,169 | 6/1995 | Roe . |
| 5,429,629 | 7/1995 | Latimer et al. . |
| 5,431,643 | 7/1995 | Ouellette et al. . |
| 5,454,801 | 10/1995 | Lauritzen . |
| 5,456,971 | 10/1995 | Fahmy . |
| 5,470,639 | 11/1995 | Gessner et al. ......................... 428/152 |
| 5,492,751 | 2/1996 | Butt, Sr. et al. . |
| 5,549,868 | 8/1996 | Carlson, II . |
| 5,562,650 | 10/1996 | Everett et al. . |
| 5,607,798 | 3/1997 | Kobylivker et al. ..................... 442/381 |
| 5,695,849 | 12/1997 | Shawver et al. ....................... 428/131 |
| 5,770,529 | 6/1998 | Dennis et al. . |

FOREIGN PATENT DOCUMENTS

WO 94/17226   8/1994   WIPO .

*Primary Examiner*—John G. Weiss
*Assistant Examiner*—Miley Craig Peppers
*Attorney, Agent, or Firm*—Alston & Bird LLP

[57] ABSTRACT

A composite nonwoven fabric is provided for use as a one-piece topsheet and barrier fabric for disposable absorbent articles including diapers, catamenial products, and adult incontinence products. The fabric is engineered to have a strikethrough region that is normally surfactant treated for receiving insults and transporting them to an absorbent core material for storage. The strikethrough region is bounded by liquid barrier regions that are suitable for defining containment structures, including diaper leg cuff. The barrier and strikethrough regions can be designed to have excellent low rewet characteristics and to have balanced properties comparable to or better than conventional spunbonded topsheet at comparable or lower basis weights.

19 Claims, 3 Drawing Sheets fig. 1.

COMPOSITE FABRIC FOR COVERSTOCK HAVING SEPARATE LIQUID PERVIOUS AND IMPERVIOUS REGIONS

CROSS REFERENCE TO RELATED APPLICATION

This application is related to and incorporates herein by reference in its entirety commonly owned copending Provisional Application Ser. No. 60/047,440, filed May 22, 1997, and claims the benefit of its earlier filing date under 35 U.S.C. 119(e).

FIELD OF THE INVENTION

This invention relates to diapers, catamenial products, and related disposable absorbent products and to the nonwoven fabrics from which these products are constructed.

BACKGROUND OF THE INVENTION

Diapers, catamenial products, adult incontinence garments, and related disposable absorbent products typically comprise a liquid pervious body side liner, which is a topsheet, a liquid impervious backing sheet, and an absorbent material disposed between the topsheet and the back sheet for storing liquid. The absorbent material typically is a pulp having particles of superabsorbent powders distributed in the pulp. The topsheet separates the wearer's skin from the absorbent material and from the liquid that is stored in the absorbent material.

It is desirable that the topsheet have rapid strikethrough so that urine, menses, water associated with feces, or other exudates of the body are rapidly brought into contact with the absorbent material and out of contact with the wearer's skin. It is also desirable that the topsheet have low rewet so that these liquids do not migrate from the absorbent layer through the topsheet and back into contact with the skin.

The topsheet is normally a nonwoven fabric prepared from relatively coarse fibers. The structure of the nonwoven fabric is controlled to provide the balance of properties desired in the topsheet of rapid strikethrough and low rewet. Typically, the nonwoven is a lightweight spunbond coverstock made from continuous filaments, usually monocomponent continuous filaments that are of sufficient denier to substantially preclude wicking of liquids stored in the absorbent core and consequent rewet. The synthetic polymeric filaments from which the topsheet is made normally are hydrophobic. Surfactants sometimes are added to the fabric to promote fluid transport for rapid strikethrough.

Diapers in particular are sometimes subjected to rapid large or repeated insults of urine and feces that sometimes exceed the strikethrough capacity of the topsheet and may exceed the absorbent capacity of the absorbent material. Modern diapers are normally designed with barrier leg cuffs that are at least somewhat impervious to liquids. The leg cuffs act as containment flaps and hold liquid in contact with the topsheet to attempt to substantially preclude leakage for a time sufficient for the liquid to strike through the top sheet and to be stored in the absorbent core.

Containment flaps may be included in the design of other absorbent garments and related products for the containment of liquids and to limit leakage. Containment flaps, including barrier leg cuffs, are normally constructed from nonwoven webs, although these barrier webs typically have different properties from coverstock intended for use as topsheet. For example, it is desirable for the wearer's comfort for the containment flaps to be liquid impervious for the containment function and to be air pervious to provide for breathability in the fabric to promote dryness and so the that the garment does not cause the wearer to feel uncomfortably hot.

An example of a composite nonwoven fabric said to be suitable for use as a barrier cuff or other containment flap is described in U.S. Pat. No. 5,492,751. This patent describes a trilaminate nonwoven fabric made from a layer of fine meltblown discontinuous fibers sandwiched between two layers of spunbond fabric.

The assembly of a diaper is somewhat problematic. The containment flaps, top sheet, absorbent core, and backsheet all have to be assembled into a single garment having distinct regions with different functions, which means that precision is needed in locating and securing the components in place. The means used to adhere the various components, which typically is hot melt adhesive, cannot be allowed to substantially detract from the functions of the different regions of the garment.

Problems have arisen in the attachment of barrier leg cuff to the diaper components. Sometimes the seal between the leg cuff and the diaper components to which the leg cuff is attached is defective, which tends to promote leakage around the leg cuff. If the topsheet has been treated to promote strikethrough with a surfactant that extends beyond the leg cuff, then liquid tends to migrate under the leg cuff and into a region sometimes referred to as the ear, where leakage can occur.

The cost to produce diapers and other disposable absorbent articles is directly related to the cost of the materials that are used to make the product and the cost of assembly of the components. The cost to produce a nonwoven fabric is directly related to the amount of polymer from which the web is made, which is to say that the cost is directly proportional to the basis weight. There is an economic incentive in coverstock production for topsheet to obtain the desired balance of strikethrough and rewet characteristics at ever reduced basis weights.

However, basis weight cannot be reduced below the point where specified properties of the fabric are lost. For example, if the basis weight is too low, then the topsheet fabric no longer has sufficient transport capability to provide the desired rapid strikethrough properties and no longer has sufficient barrier capability to provide the desired low rewet properties. Too low basis weight tends to result in migration of superabsorbent particles across the topsheet into contact with the wearer's skin. Too low basis weight also tends to result in glue bleed through in which adhesive penetrates the topsheet and precludes construction of a satisfactory assembly.

Efforts have been made to prepare topsheet that has regions of liquid permeability and liquid impermeability so that, for example, a diaper or catamenial product has a topsheet region providing for strikethrough, but is liquid impermeable outside this region for liquid containment in the absence of leakage. For example, U.S. Pat. No. 5,431,643 describes a topsheet for use in feminine napkins wherein the topsheet has areas of liquid permeability and areas of liquid impermeability. The impervious areas are formed after the fabric has been produced by application of an impervious coating to selected regions of the fabric by a silk screen printing operation. However, the impervious coating renders the fabric with little or no breathability in the coated areas.

U.S. Pat. No. 5,456,971 describes a compound nonwoven web intended for use as a topsheet in diapers and the like in which the web is formed with separate regions within a single layer for liquid permeability and liquid impermeability. Fine and coarse filaments, which can be meltblown and spunbond filaments, respectively, are admixed with no discrete phase boundary so as to form the liquid impermeable regions. The compound web differs in this respect from a composite fabric structure made of more than one layer. The compound web structure allows fine fibers to contact the skin of the wearer, which could promote wicking of liquid from the absorbent material and consequent undesirable rewet performance.

Design and assembly of diapers and related products would be greatly simplified and the costs of production would be reduced if a single fabric could be satisfactorily used at relatively low basis weight for both containment and liquid permeable topsheet that did not have the above noted drawbacks and disadvantages. It would be desirable to produce a fabric that had separate regions for strikethrough and barrier, could be used in assemblies that were not prone to leakage, and that had a balance of properties so that the strikethrough region had acceptable low rewet characteristics and the barrier region had acceptable breathability and low rewet.

SUMMARY OF THE INVENTION

The invention comprises a composite nonwoven structure in which the physical properties of the composite nonwoven structure are manipulated to cause the structure to have good strikethrough and rewet characteristics in selected regions of the fabric while maintaining barrier properties in other regions of the fabric without sacrificing breathability. The composite nonwoven structure is useful as coverstock for disposable absorbent articles and can be used to form a one piece topsheet and barrier fabric for use in diapers. Barrier leg cuffs and other containment structures or barrier zones can be formed in the composite nonwoven fabric adjacent the strikethrough portions of the fabric for simplified garment construction and in the absence of leakage.

The barrier regions can be formed by judicious placement of fine fibers having barrier characteristics within the composite. Alternatively, the entire composite can be prepared as a barrier fabric and the structure can be treated with a suitable surfactant to permit fluid flow in selected regions. Capillary movement within the fluid flow region can be achieved by choice of filament diameters and by controlling the size of the pores formed between adjacent filaments.

In one embodiment of the invention, the composite nonwoven structure is a spunbond-meltblown-spunbond trilaminate structure in which a layer of substantially discontinuous meltblown polymeric fiber is sandwiched between two layers of spunbond continuous filaments. This structure has superior fluid barrier properties at equal basis weights in comparison to fabrics made only of spunbonded filaments. While not wishing to be bound by theory, it is believed that the finer meltblown fibers bridge the voids between the much larger spunbonded filaments to produce improved fluid barrier properties by reducing effective pore size. A surfactant is selectively applied to the fabric to create the fluid flow regions and to promote strikethrough.

In another embodiment, a composite structure is produced in which substantially discontinuous meltblown polymeric fiber is selectively placed between layers of spunbond. A composite fabric is produced that has barrier properties in selected regions in which meltblown is present. For example, the meltblown fibers can be deposited in longitudinal stripes that extend the length of the spunbond layer in the machine direction. The regions without meltblown fibers do not have the barrier properties typically associated with a spunbond-meltblown-spunbond trilaminate structure. A surfactant can be selectively applied to the fabric in the regions in the absence of meltblown to create the fluid flow regions and to promote strikethrough.

In additional embodiments, although not necessarily with equivalent results, the composite nonwoven fabric can be produced with a single layer of spunbond and a layer of meltblown deposited thereon either as a continuous layer or in longitudinal stripes that extend the length of the spunbond layer in the machine direction. In this embodiment, the fabric is oriented in disposable absorbent articles so that the spunbond layer faces the skin of the wearer and the meltblown layer faces the absorbent material so as to reduce the likelihood of rewet.

It should be recognized that the barrier stripes can alternated with coarse spunbond stripes between the barrier stripes, if desired, in any of the composites of the invention. It should be recognized that either the barrier stripes or the continuous layer of barrier can comprise fine continuous spunbond filaments that have barrier properties. Typically, these filaments are of less than one denier, whereas more coarse spunbond filaments are used in the layers facing the skin to substantially reduce wicking and rewet. Mixtures of meltblown and spunbond having sufficient barrier properties can be used in compound web regions within the composite structure.

In another embodiment, the invention provides a topsheet suitable for a diaper or other disposable absorbent article that can be produced with a central region that has the characteristics of rapid strikethrough and low rewet for distribution of body fluids to the absorbent layer. A peripheral region outside the central region can retain its barrier properties sufficient to be useful as a containment flap, leg cuff, or barrier zone so as to substantially preclude leakage of body fluids.

Thus, the invention provides, among other things, a nonwoven fabric that is suitable for use as a one-piece topsheet and barrier fabric in which a single fabric is used for both leg cuff and topsheet. The invention substantially eliminates the need for separate containment flaps applied to a topsheet and also provides a breathable fabric.

BRIEF DESCRIPTION OF THE DRAWINGS

Some of the objects and advantages of the invention have been stated. Others will appear as the description proceeds when taken in conjunction with the accompanying drawings in which.

DETAILED DESCRIPTION OF THE INVENTION

Figure 1:
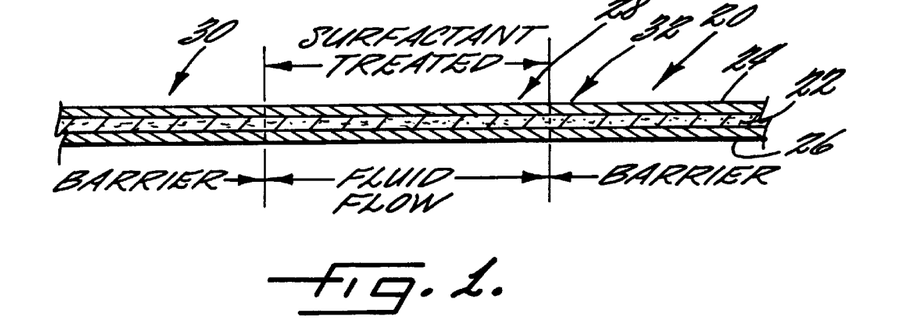
FIG. 1 is a cross sectional view representing one embodiment of a nonwoven composite fabric of the invention.

FIG. 1 is a cross-sectional view representing an embodiment of a nonwoven composite fabric 20 of the invention that is suitable coverstock for use as topsheet for disposable absorbent articles, including, for example, diapers, adult incontinence products, and catamenial products. The nonwoven composite fabric shown in FIG. 1 is of a spunbond/meltblown/spunbond trilaminate construction (SMS) in which a layer of substantially discontinuous meltblown polymeric fibers 22 is sandwiched between layers 24, 26 of substantially continuous spunbond polymeric filaments. Methods of making SMS webs are generally known in the art and should be apparent to the skilled artisan. In accordance with the invention, selected portions of the fabric are treated with a surfactant to establish a strikethrough zone 28 that provides for fluid flow through the fabric. Those regions of the fabric that are not treated with surfactant retain their barrier properties and provide barrier regions 30 and 32.

The nonwoven composite fabric of the invention has separate regions with separate functions that should be balanced for optimum performance as a one-piece topsheet and barrier fabric. The surfactant treated regions of the fabric should have rapid strikethrough to promote fluid flow while the adjacent regions have barrier properties to substantially eliminate fluid flow. Low rewet is of concern over the entire fabric since it is desirable that none of the fabric wick moisture from the absorbent core of a disposable absorbent article to the surface of the topsheet and into contact with the wearer's skin.

The balance of strikethrough and rewet performance for a given basis weight is related to the diameter of discontinuous fibers and to the denier, or length-per-unit-weight, of the continuous filaments. Coarse meltblown filaments of from about 2 to 15 microns in diameter have been determined to provide a suitable balance of strikethrough in the surfactant treated areas, barrier in the untreated areas, and low rewet in accordance with the invention. A range of from 6 to 10 microns is somewhat more typical. Too large filaments tend to provide insufficient barrier and too small filaments tend to provide insufficient strikethrough when the meltblown is present in the strikethrough regions of the fabric.

The coarse spunbond continuous filaments made from polypropylene or blends of polypropylene with polyethylene typically will have a denier in the range of from about 1½ to 3½, somewhat more typically from about 2½ to 3½ denier. If the filaments are much coarser than 3½ denier, then the spunbond layers of the fabric will not offer sufficient barrier to superabsorbent polymer particles that are typically contained within the absorbent core of a disposable absorbent article. These particles can migrate through the coverstock, adhere to the skin of the wearer, and swell in the presence of liquid in a phenomenon known as "gel-on-skin," which is considered undesirable from aesthetic standpoint.

The substantially continuous polymeric spunbond filaments and the substantially discontinuous meltblown polymeric fibers can be prepared from a wide variety of thermoplastic polymers. Polypropylene polymer is often used to prepare meltblown fibers and spunbond filaments. A small amount of polyethylene polymer can be included in the polymer blend from which the filaments and fibers are prepared. Less than 10 percent of polyethylene in the blend, and typically around 4 percent by weight of polyethylene in the blend, can improve the bonding of the various layers of an SMS construction because of the presence of a small amount of the lower melting polyethylene polymer. It should be recognized that some of the more specialized polymers that have been developed may be useful for preparing the meltblown or spunbond fibers. Particular polymers include the various polymer alloys, high elongation polymers, Catalloys, and others that can be used in blends or in bicomponent filaments in which two or more polymeric components are included in separate regions in the cross-section of a filament.

The balance of properties desirable in the composite nonwoven fabric of the invention is also related to the basis weight of the individual webs used in the fabric and to the overall weight of the fabric. A desirable balance of strikethrough, barrier, and rewet performance can be achieved in fabrics of the invention at basis weights comparable to and even less than a conventional single layer continuous filament spunbond topsheet. For example, the nonwoven composite fabric can have an overall basis weight of from about 13 to 22 gsm, more typically from about 16 to 22 gsm.

Figure 2:
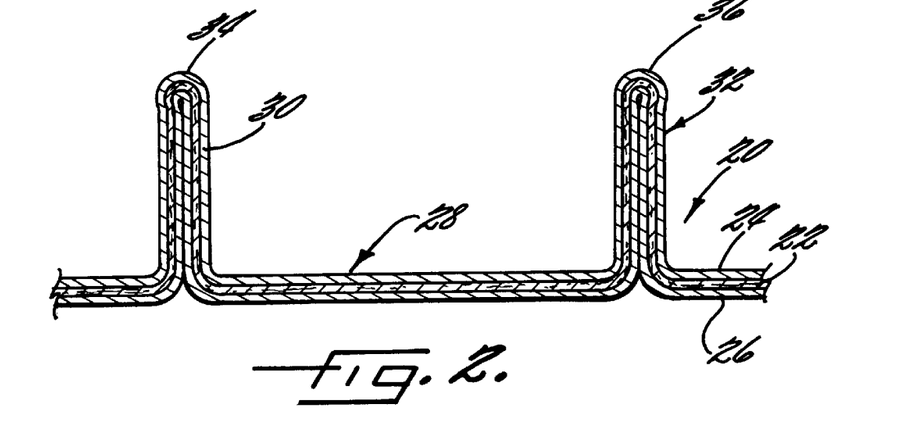
FIG. 2 is a cross sectional view of the embodiment of FIG. 1 folded to create a containment structure.

The spunbond and meltblown web components of the composite nonwoven fabric can be present in a ratio of from about 11 gsm to 1.5 gsm, respectively, up to about 19 gsm to 3 gsm. Somewhat more typically, the ratio is from about 13:2 to 19:2. Too much meltblown fiber can adversely impact strikethrough in the embodiment of FIG. 1, and it should be recognized that when the barrier regions 30 and 32 are folded to create leg cuff structures 34 and 36, respectively, as illustrated in FIG. 2, then the layers of meltblown are folded and are of double thickness in these regions and still of a single thickness in the strikethrough, surfactant-treated, liquid flow region. The continuous filament spunbond layers are typically of equal basis weight for convenience, but need not necessarily be so for performance.

The surfactant that is applied to establish the strikethrough regions of the fabric typically will be a standard, nondurable surfactant that is designed to provide hydrophilicity essentially for a single insult. Standard, nondurable surfactants are applied in accordance with the invention in amounts ranging from about 0.15% to 0.4% by weight of the fabric. Somewhat more typically, the nondurable surfactants can be applied in amounts of from about 0.25% to 0.33% by weight to achieve the desired balance between rapid strikethrough and low rewet performance. Suitable nondurable surfactants include Silwet Y-12037, which is available from Witco Corporation in Tarrytown, N.Y. Silwet Y-12037 has more recently been sold as Nuwet 237.

It should be recognized that more durable surfactant finishes can be applied to the topsheet in accordance with the invention, if desired, although not necessarily with equivalent results. A suitable example of a durable surfactant is Nuwet 350, which is also available from Witco. Semidurable and durable surfactant finishes typically require more surfactant than does a nondurable finish. Durable finishes designed for strikethrough of multiple insults are normally applied in amounts of up to about 0.5 to 1.0% by weight, more typically from about 0.6 to 0.7% by weight. Standard finishes applied at these amounts could be expected to result in poor rewet performance.

The surfactant can be applied by any of the several methods known to the skilled artisan, including by application of a foam in which the surfactant is carried or by spraying the surfactant, although not necessarily with equivalent results in fabric performance. If the surfactant is applied by foaming, then it should be recognized that a small amount of a foaming agent normally is mixed with the surfactant for more effective introduction of air into the surfactant. A suitable foaming agent is Carsonol SLS-S, which is offered by Lonza Company, which is located in Fair Lawn, N.J.

The surfactant can be applied to the nonwoven composite fabric of the invention as stripes placed along the fabric in the machine direction or as discreet regions, usually ovals, that will define the strikethrough regions of a completed disposable absorbent article. The surfactant can be applied to the coverstock roll goods at the absorbent article manufacturer's plant. Some diaper forming lines have the capability to apply surfactants and other fluids to the coverstock inline and in proper registry as the diapers are manufactured. Alternatively, the surfactant can be applied by the roll goods manufacturer, typically after the nonwoven composite fabric has been bonded and normally as stripes that run the length of fabric in the machine direction.

The amounts in which particular surfactants are used should be empirically determined and can vary according to the type of surfactant, additional foamers or other agents that are included in the surfactant formulation, the method of surfactant application, and the specific construction of the disposable absorbent article in which the surfactant will be used.

Figure 3:
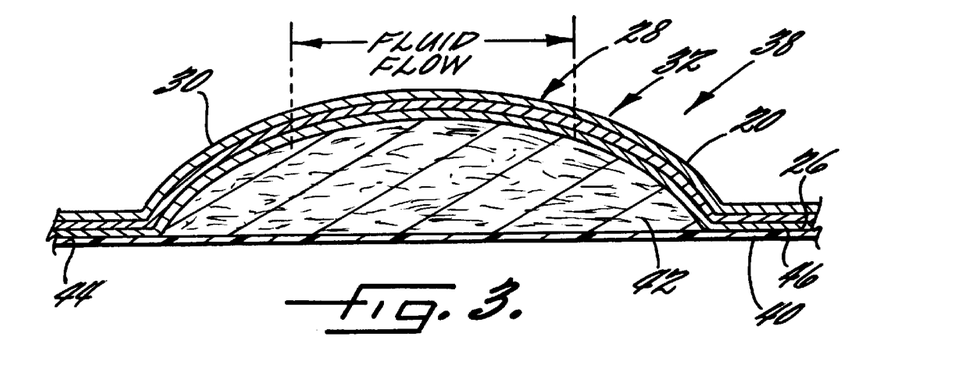
FIG. 3 is a cross sectional view of an absorbent garment structure showing the embodiment of FIG. 1 as a topsheet in assembly with a back sheet and an absorbent core disposed between the topsheet and the back sheet.

Turning now to FIG. 3, FIG. 3 represents a cross section through a disposable absorbent article, shown generally at 38 and depicting the nonwoven composite fabric of FIG. 1 in the environment in which it is used. The disposable absorbent article comprises a topsheet 20 in accordance with the invention as represented in FIG. 1, a liquid impervious back sheet 40, and a core of absorbent material 42 between the topsheet and the back sheet. The back sheet and topsheet are laminated together at 44 and 46 by suitable means. The spunbond layer 26 is useful for providing adherence between the topsheet and the bottom sheet. The strike through region providing for fluid flow into the absorbent core is shown at 28, bounded by barrier regions 30 and 32.

It should be recognized that the skilled artisan can produce topsheet in accordance with the invention in a number of alternative embodiments and by a number of alternative methods, keeping in mind the principles above elucidated of separate strikethrough and barrier regions having balanced properties. FIGS. 1, 2 and 3 represent an SMS construction. An alternative embodiment is represented in cross section in FIG. 4 in which the meltblown layer 22' is discontinuous across the width of the composite nonwoven fabric 20'. Otherwise, the fabric is similar to that of FIG. 1 and can be used similarly as illustrated in FIGS. 2 and 3. In FIG. 2, the fabric has been folded to create a containment structure that bounds the liquid transport region on two sides. Similar portions of the composite nonwoven fabric of FIG. 4 are numbered similarly to FIG. 1 and are indicated as primes.

Figure 4:
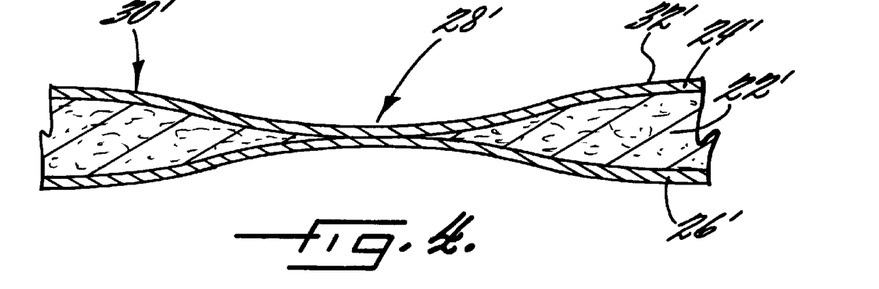
FIG. 4 is a cross sectional view representing another embodiment of a nonwoven composite fabric of the invention.

The regions of the composite of FIG. 4 containing meltblown, 30' and 32', define the barrier regions of the composite. The regions containing only the spunbond layers 26' and 24' define the strikethrough region of the fabric 28', which typically is surfactant treated as discussed in connection with the embodiment of FIG. 1, since the thermoplastic polymeric continuous filamentary webs typically are hydrophobic if untreated with a surfactant.

Figure 5:
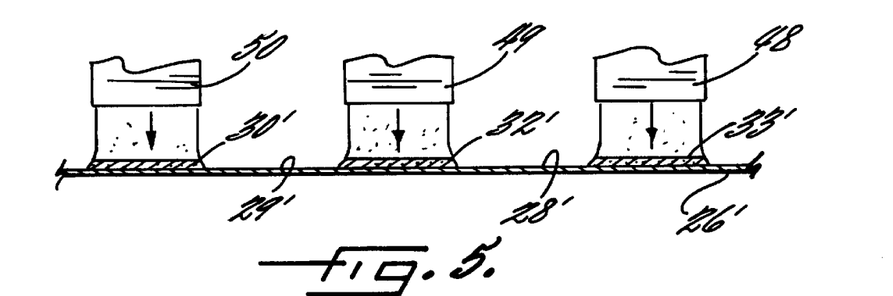
FIG. 5 is a cross sectional view of the embodiment of FIG. 4 prior to completion of the composite structure and representing one embodiment for making the composite.

FIG. 5 represents a cross section in the machine direction of one embodiment of a method for preparing the composite nonwoven fabric of FIG. 4 in which the meltblown regions of the fabric 30', 32', and 33' are laid down in stripes on a previously laid continuous filament web, 26' that will ultimately define the barrier regions of the fabric after the assembly and bonding of the composite are completed and the strikethrough regions are surfactant treated. The regions 28' and 29' have an absence of meltblown and define the strikethrough regions of the fabric.

It should be recognized that fine meltblown fibers of less than two microns can be used in these selected regions of the fabric to provide barrier, if desired. However, these finer fibers typically would not have the strikethrough properties that would be desirable for use in the fluid flow regions of the fabric.

Apparatus for laying down individual meltblown stripes is represented in FIG. 5 at 48, 49, and 50. A spunbond continuous filamentary web 24', in accordance with the embodiment illustrated in FIG. 4 could be added in line downstream of the application of the discontinuous fiber meltblown regions in the manner in which SMS fabrics normally are prepared, after which the fabric is bonded, usually by the application of heat and pressure via calender rolls. It should be recognized that there are a number of methods for bonding the composite fabric, including through air bonding and others that can be selected depending upon the properties desired in the completed composite.

Figure 6:
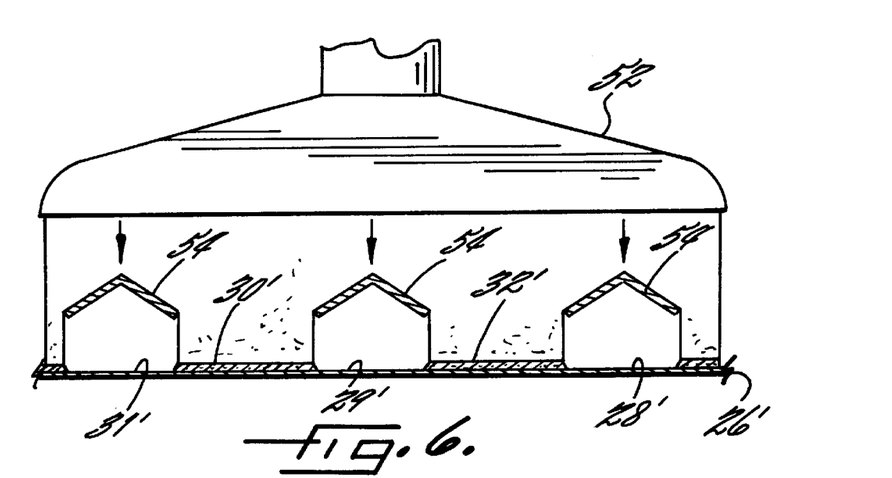
FIG. 6 is a cross sectional view of the embodiment of FIG. 4 prior to completion of the composite structure and representing another embodiment for making the composite.

An alternative method is illustrated in FIG. 6 in which a single apparatus 52 for laying down separate discontinuous fiber meltblown regions 30' and 32' is illustrated. The fibers are laid down over the entire width of the spunbond filamentary web 26'. Separate regions of meltblown alternating with regions in the absence of meltblown 28', 29', and 31' are formed by baffles 54 that direct the fibers into the meltblown regions and preclude their deposition in the areas that will define the strikethrough regions of the completed composite fabric.

Figure 7:
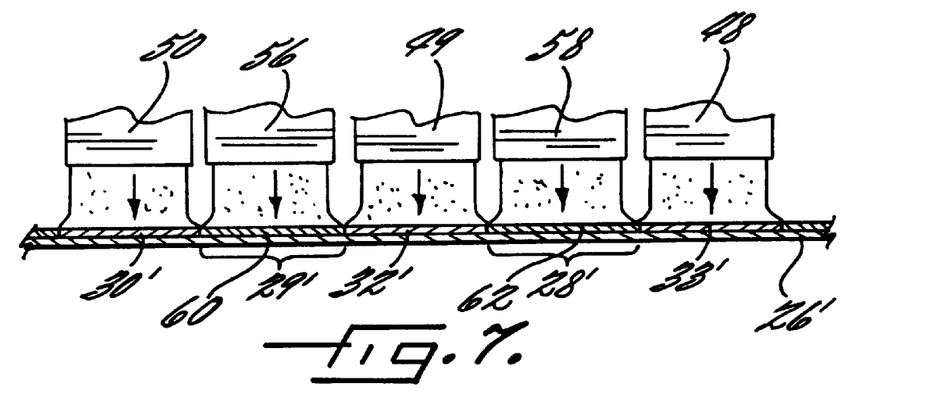
FIG. 7 is a cross sectional view of another embodiment of the invention prior to completion of the composite structure and representing another embodiment for making the composite.

Another alternative method for forming another embodiment of the invention is represented in FIG. 7. In FIG. 7, the discontinuous fiber meltblown regions defining the barrier regions 30' and 32' are produced as in FIG. 5. Fine meltblown barrier fibers of less than 2 microns diameter are laid down to define barrier regions 30', 32', and 33'. More coarse meltblown fibers are laid down in regions 60 and 62 from apparatus 56 and 58, respectively, that are suitable for providing a balance of strikethrough and low rewet when the composite is treated with surfactant. These fibers are normally in the range of from about 2 to 15 microns in diameter, although the range of from about 6 to 10 microns is somewhat more typical. It should be recognized that fibers of these diameters could also be used in the barrier regions of the fabric as described in connection with FIG. 1.

It should be recognized that each of the embodiments represented in FIGS. 1 through 7 can be produced as spunbond and meltblown laminates in the absence of an additional spunbond layer sandwiching the meltblown. However, the composite fabric in this embodiment should be orientated in the disposable absorbent article of FIG. 3 so that the spunbond layer faces the skin, on the outermost layer of the article, which is shown in FIG. 3 as layer 24. The relatively coarse spunbond continuous filaments substantially preclude wicking from the absorbent core to provide the desired low rewet performance over both the strikethrough and barrier regions of the composite.

It should also be recognized that the capability exists for producing subdenier continuous filamentary webs, which is of denier less than 1, that have barrier properties and could be substituted for the meltblown regions of FIGS. 1 through 7. Methods for producing these filaments are shown in copending patent application U.S. Ser. No. 08/681,244, filed Jul. 22, 1996 for Meltspun Multicomponent Thermoplastic Continuous Filaments, Products Made Therefrom, and Methods Therefor.

Normally, several individual attenuators distributed across the width of the web would be more convenient than single slot attenuators for depositing separate regions of spunbond filaments for the barrier regions of FIG. 5 or for depositing barrier regions alternating with strikethrough regions as shown in FIG. 7. Slot attenuators would be useful in connection with the embodiment of FIG. 1 prepared with a central spunbond web instead of discontinuous fibers since the web extends across the width of the outer coarse spunbond webs.

The barrier regions represented in FIGS. 1 through 7 could also be produced with mixtures of substantially continuous filaments and discontinuous fibers instead of the meltblown fibers that have been above discussed in connection with the invention to achieve similar results in barrier, strikethrough, and low rewet performance. Methods for creating mixtures of spunbond and meltblown webs are believed to be within the purview of the skilled artisan.

The attached Table 1 shows five trilaminate fabrics prepared in accordance with the invention. These fabrics were evaluated for use as a combined top sheet and barrier fabric having a hydrophilic center and hydrophobic edges. The samples evaluated were 4% polyethylene fabrics at 14/3, 17/3, 17/2, and 19/2 spunbond/meltblown basis weights as well as a 100% polypropylene fabric at 19/2 spunbond meltblown basis weight. Surfactant was applied by foaming at a level of 0.28% by weight of the fabric for Example 1. The surfactant application was made at a level of 0.20% and at 0.28% for each fabric sample 2 through 5 using Silwet Y-12037 with Carsonol SLS-S foaming agent. The fabric was treated with surfactant in an oval pattern to create a zone that has good liquid transport and rewet properties. However, outside this zone, the fabric acts as a barrier.

TABLE I

| | Example | | | | | | | | |
|---|---|---|---|---|---|---|---|---|---|
| | 1 | 2 | | 3 | | 4 | | 5 | |
| Spunbond (gsm) | 14 | 17 | | 17 | | 19 | | 19 | |
| Meltblown (gsm) | 3 | 3 | | 2 | | 2 | | 2 | |
| Composition | 4% PE | 4% PE | | 4% PE | | 4% PE | | 100% PP | |
| Surfactant Level (%) | 0.28 | 0.28 | 0.20 | 0.28 | 0.20 | 0.28 | 0.20 | 0.28 | 0.20 |
| Basis Weight (gsm) | 17.43 | 20.10 | 20.14 | 19.58 | 19.69 | 21.26 | 21.15 | 21.48 | 21.33 |
| Strike-Through (sec) | 1.94 | 2.12 | 3.61 | 1.96 | 2.61 | 1.94 | 3.16 | 2.10 | 2.98 |
| Rewet (grams) | 1.42 | 1.46 | 1.09 | 1.15 | 0.91 | 0.93 | 0.54 | 0.58 | 0.53 |
| RCST (mm)[1] | 122.7 | 176.1 | 204.4 | 156.6 | 151.6 | 143.4 | 150.8 | 197.6 | 165.8 |

[1]RCST values tested on the untreated, hydrophobic portions of the webs

The data in Table I show that the rewet values were high with respect to typical industry diaper topsheet requirements, even at the reduced surfactant level of 0.20%, for the standard rewet test. However, when the fabric of the invention was placed in a diaper construction, as shown in Table II, below, the rewet values were surprisingly comparable to or better than those for commercial diapers for fabrics of comparable or lower basis weight. The rising column strikethrough (RCST) test demonstrated that the barrier property of the hydrophobic area of the fabric was preserved.

Table II shows data for commercially purchased diapers that were evaluated in comparison to the composite topsheets of the invention. The existing topsheets of the purchased diapers were removed and replaced with each of the materials listed in Table II and the diapers were then subjected to multiple insults of synthetic urine liquid. Each diaper was subjected to two insults at 100 ml per insult. The strike-through time for each of the insults and the rewet level after each of the insults were evaluated for each of the selected materials.

TABLE II

| | TRILAMINATE COMPOSITE DIAPER TOPSHEET (0.28% Surfactant) | | | | | | | | | | | | | | | CONTROL DIAPER | | | | | |
| | | | | | | | | | | | | | | | | Control Diapers Topsheet | | | | | |
| | 14/3 SB/MB 4% PE | | | 17/3 SB/MB 4% PE | | | 17/2 SB/MB 4% PE | | | 19/2 SB/MB 5% PE | | | 19/2 SB/MB 100% PP | | | Control Diapers As Purchased | | | Removed & Replaced | | |
| Description | Avg. | S.D. | N | Avg. | S.D. | N | Avg. | S.D. | N | Avg. | S.D. | N | Avg. | S.D. | N | Avg. | S.D. | N | Avg. | S.D. | N |
|---|---|---|---|---|---|---|---|---|---|---|---|---|---|---|---|---|---|---|---|---|---|
| Diaper Strike-Through (sec) | | | | | | | | | | | | | | | | | | | | | |
| @ 100 ml | 9.81 | 1.97 | 8 | 10.41 | 0.90 | 8 | 9.86 | 0.67 | 8 | 10.64 | 1.53 | 8 | 9.59 | 1.33 | 8 | 12.49 | 1.56 | 8 | 13.19 | 1.07 | 8 |
| @ 200 ml | 16.51 | 3.99 | 8 | 21.83 | 5.26 | 8 | 17.75 | 3.28 | 8 | 17.86 | 3.84 | 8 | 16.94 | 3.35 | 8 | 17.68 | 4.52 | 8 | 20.83 | 3.24 | 8 |
| Diaper Rewet (grams) | | | | | | | | | | | | | | | | | | | | | |
| @ 100 ml | 0.34 | 0.12 | 8 | 0.44 | 0.05 | 8 | 0.41 | 0.02 | 8 | 0.43 | 0.01 | 8 | 0.40 | 0.01 | 8 | 0.40 | 0.01 | 8 | 0.40 | 0.02 | 8 |
| @ 200 ml | 17.07 | 2.28 | 8 | 15.76 | 2.94 | 8 | 14.73 | 2.27 | 8 | 15.94 | 1.19 | 8 | 12.83 | 2.67 | 8 | 11.80 | 6.57 | 8 | 18.05 | 4.02 | 8 |

As can be seen from Table II, the first insult strike-through times for all materials evaluated were equal to or better than that for the control diapers as received and with the top sheet removed and replaced. The topsheet was removed and replaced on one set of controls to understand the effect of the remove and replace procedure and to more closely represent the performance of the test materials. The second insult strike-through times for the second insult were equal to or better than that for the control diapers for all materials except the 17/3 SB/MB fabric. The first insult rewet values for all materials evaluated were comparable to those for the control diapers as received and with the topsheet removed and replaced with the 17/3 and 19/2, 4% PE fabrics testing slightly higher. The second insult rewet values for all materials evaluated were better than that for the control diapers with the top sheet removed and replaced although not as good as seen with the control diapers as received.

Tables III and IV below compare the performance of several examples of SMS fabric of the invention to standard continuous filament topsheet fabrics and control diapers from the standpoints of basis weight, strikethrough, rewet, and rising column strikethrough (RCST), which is a measure of barrier properties. Examples of fabrics of the invention were compared that used fine meltblown of about 2.5 microns with coarse meltblown of about 5 to 8 microns. Increasing the meltblown fiber diameter to the 5 to 8 micron range reduced the barrier properties of the composite fabric as measured across the full unit doff width before surfactant treating. However, in a one-piece topsheet having a leg cuff formed therein, the fabric would be doubled in the leg cuff region, which would increase the barrier property. The increased meltblown diameter provided improved strikethrough performance after application of a standard nondurable or durable surfactant. Choice of surfactant is not believed to impact these results. However, it is believed that a durable surfactant would significantly increase diaper performance under heavy or repeated insults.

In Table IV, samples of the fabrics of the invention were substituted for the original topsheet in Pampers Baby-Dry brand diapers for boys and girls and in Ultra Dry Thin Walker 2 brand diapers for boys. The former has a spunbond topsheet and overall curly pulp core; the latter had a carded topsheet and localized curly pulp core. The latter showed higher rewet values, generally, for the second insult that is believed to be due to the control diaper design. The first insult of 100 ml of synthetic urine showed comparable rewet between the fabrics of the invention and the spunbond controls and much better rewet and strikethrough than the carded control on the second insult.

TABLE III

| | Sample | | | | | | | | | | | |
| | 1 | | | 2 | | | 3 | | | 4 | | |
| | 13.5/2 Fine MB Silwet Treated | | | 13.5/2 Coarse MB Silwet Treated | | | 13.5/2 Coarse MB Nuwet 350 Treated | | | 15.1/2.2 Coarse MB Silwet Treated | | |
| Description | Avg. | S.D. | N | Avg. | S.D. | N | Avg. | S.D. | N | Avg. | S.D. | N |
|---|---|---|---|---|---|---|---|---|---|---|---|---|
| Basis Weight (gsm) | 15.8 | 1.2 | 12 | 15.8 | 0.9 | 12 | 15.8 | .09 | 12 | 17.3 | .08 | 12 |
| Strike-Through (sec) | 3.36 | 0.39 | 10 | 2.63 | 0.28 | 10 | 2.79 | 0.28 | 10 | 2.74 | 0.33 | 10 |
| Rewet (grams) | 0.93 | 0.38 | 10 | 0.19 | 0.09 | 10 | 0.15 | 0.05 | 10 | 0.12 | 0.02 | 10 |
| Diaper Strike-Through (sec) | | | | | | | | | | | | |
| @ 100 ml | 10.02 | 0.73 | 6 | 9.40 | 0.79 | 5 | 10.15 | 1.54 | 5 | 10.47 | 0.71 | 5 |
| @ 200 ml | 25.26 | 3.48 | 5 | 22.90 | 2.90 | 5 | 25.56 | 4.09 | 5 | 19.73 | 5.01 | 5 |

TABLE III-continued

| | Sample | | | | | | | | | | | |
|---|---|---|---|---|---|---|---|---|---|---|---|---|
| | 1 | | | 2 | | | 3 | | | 4 | | |
| Diaper Rewet (grams) | | | | | | | | | | | | |
| @ 100 ml | 0.34 | 0.01 | 6 | 0.34 | 0.01 | 5 | 0.34 | 0.02 | 5 | 0.34 | 0.02 | 5 |
| @ 200 ml | 22.03 | 3.86 | 5 | 12.26 | 5.01 | 5 | 8.94 | 3.26 | 5 | 4.22 | 5.03 | 5 |
| RCST (mm) | | | | | | | | | | | | |
| Full width | 179 | 42 | 12 | 72 | 13 | 12 | 72 | 13 | 12 | 81 | 21 | 12 |
| Adjacent to Philic Area | 178 | 33 | 10 | 68 | 12 | 10 | 64 | 7 | 10 | 96 | 15 | 10 |
| Spunbond Diameter (dpf) | | | | | | | | | | | | |
| Full Width Unit Doff | 2.73 | 0.28 | 30 | 2.61 | 0.20 | 30 | 2.61 | 0.20 | 30 | 2.68 | 0.23 | 30 |
| Surf. Treated Roll | 2.63 | 0.26 | 10 | 2.58 | 0.19 | 10 | 2.58 | 0.19 | 10 | 2.52 | 0.24 | 10 |
| Meltbown Dia. (microns) | | | | | | | | | | | | |
| Full Width Unit Doff | 2.5 | 1.1 | 15 | 8.2 | 4.1 | 15 | 8.2 | 4.1 | 15 | 5.0 | 1.9 | 15 |
| Surf. Treated Roll | 2.5 | 1.5 | 5 | 7.3 | 2.0 | 5 | 7.3 | 2.0 | 5 | 6.3 | 2.5 | 5 |

| | Control Fabric 1 | | | Control Fabric 2 | | | Commercial Diaper Control (With Spunbond Topsheet) | | | | | |
|---|---|---|---|---|---|---|---|---|---|---|---|---|
| | 050MXPV09O (Silwet Treated) | | | 0.65MXPV09O (Silwet Treated) | | | Topsheet Removed and Replaced | | | As Purchased | | |
| Description | Avg. | S.D. | N | Avg. | S.D. | N | Avg. | S.D. | N | Avg. | S.D. | N |
| Basis weight (gsm) | 17.8 | — | 1 | 22.4 | — | 1 | N/A | | | N/A | | |
| Strike-Through (sec) | 3.41 | 0.65 | 10 | 2.82 | 0.61 | 10 | N/A | | | N/A | | |
| Rewet (grams) | 0.09 | 0.01 | 10 | 0.09 | 0.01 | 10 | N/A | | | N/A | | |
| Diaper Strike-Through (sec) | | | | | | | | | | | | |
| @ 100 ml | 9.26 | 0.90 | 5 | 9.68 | 0.97 | 5 | 7.57 | 0.88 | 5 | 6.92 | 0.69 | 5 |
| @ 200 ml | 20.03 | 5.60 | 5 | 21.65 | 2.74 | 5 | 17.50 | 7.72 | 5 | 20.34 | 3.47 | 5 |
| Diaper Rewet (grams) | | | | | | | | | | | | |
| @ 100 ml | 0.33 | 0.02 | 5 | 0.31 | 0.01 | 5 | 0.32 | 0.01 | 5 | 0.33 | 0.01 | 5 |
| @ 200 ml | 7.43 | 3.32 | 5 | 0.64 | 0.41 | 5 | 4.21 | 2.80 | 5 | 3.20 | 1.35 | 5 |
| RCST (mm) | | | | | | | | | | | | |
| Full width | N/A | | | N/A | | | N/A | | | N/A | | |
| Adjacent to Philic Area | | | | | | | | | | | | |
| Spunbond Diameter (dpf) | | | | | | | | | | | | |
| Full Width Unit Doff | N/A | | | N/A | | | N/A | | | N/A | | |
| Surf. Treated Roll | | | | | | | | | | | | |
| Meltbown Dia. (microns) | | | | | | | | | | | | |
| Full Width Unit Doff | N/A | | | N/A | | | N/A | | | N/A | | |
| Surf. Treated Roll | | | | | | | | | | | | |

TABLE IV

| | 15.1/2.2 Coarse MB Silwet Treated | | | Control Diapers Topsheet Removed & Replaced Spunbond Topsheet | | | 15.1/2.2 Coarse MB Silwet Treated | | | Control Diapers Topsheet Removed & Replaced Carded Topsheet | | |
|---|---|---|---|---|---|---|---|---|---|---|---|---|
| Description | Avg. | S.D. | N | Avg. | S.D. | N | Avg. | S.D. | N | Avg. | S.D. | N |
| Basis Weight (gsm) | | | | | | | | | | | | |
| Full Width Unit Doff | 17.3 | 0.8 | 12 | N/A | | | 17.3 | 0.8 | 12 | N/A | | |
| Strikethrough Samples | 17.3 | 1.1 | 10 | | | | N/A | | | | | |
| Strike-Through (sec) | 2.74 | 0.33 | 10 | N/A | | | N/A | | | N/A | | |
| Rewet (grams) | 0.12 | 0.02 | 10 | N/A | | | N/A | | | N/A | | |
| 1 | | | | | | | | | | | | |
| Diaper Strike-Through (sec) | | | | | | | | | | | | |
| @ 100 ml | 10.47 | 0.71 | 5 | 7.57 | 0.88 | 5 | 13.08 | 1.01 | 5 | 11.00 | 1.36 | 5 |
| @ 200 ml | 19.73 | 5.01 | 5 | 17.50 | 7.72 | 5 | 28.98 | 3.70 | 5 | 23.22 | 14.12 | 5 |

TABLE IV-continued

| Description | 15.1/2.2 Coarse MB Silwet Treated | | | Control Diapers Topsheet Removed & Replaced Spunbond Topsheet | | | 15.1/2.2 Coarse MB Silwet Treated | | | Control Diapers Topsheet Removed & Replaced Carded Topsheet | | |
|---|---|---|---|---|---|---|---|---|---|---|---|---|
| | Avg. | S.D. | N | Avg. | S.D. | N | Avg. | S.D. | N | Avg. | S.D. | N |
| Diaper Rewet (grams) | | | | | | | | | | | | |
| @ 100 ml | 0.34 | 0.02 | 5 | 0.32 | 0.01 | 5 | 0.32 | 0.01 | 5 | 0.34 | 0.02 | 5 |
| @ 290 ml 2 | 4.22 | 5.03 | 5 | 4.21 | 2.80 | 5 | 7.49 | 3.75 | 5 | 14.12 | 6.03 | 5 |
| RCST (mm) | | | | | | | | | | | | |
| Full Width | 81 | 21 | 12 | N/A | | | N/A | | | N/A | | |
| Adjacent to Philic Area | 96 | 15 | 10 | | | | | | | | | |
| Spunbond Diameter (dpf) | | | | | | | | | | | | |
| Full Width Unit Doff | 2.68 | 0.23 | 30 | N/A | | | N/A | | | N/A | | |
| Surf. Treated Roll | 2.52 | 0.24 | 10 | | | | | | | | | |
| Meltblown Dia. (microns) | | | | | | | | | | | | |
| Full Width Unit Doff | 5.0 | 1.9 | 15 | N/A | | | N/A | | | N/A | | |
| Surf. Treated Roll | 6.3 | 2.5 | 5 | | | | | | | | | |

The invention has been described in the drawings and in the specification with respect to specific embodiments. Although specific terms are employed, they are used in a generic and descriptive sense only and not for purposes of limitation, the scope of the invention being defined in the claims.

What is claimed is:

1. Coverstock for a disposable absorbent article, said coverstock comprising a nonwoven composite bonded fabric structure having a liquid transport region for strikethrough of liquid through the surface thereof bounded on at least one side thereof by a liquid barrier region, said liquid barrier region of said nonwoven composite bonded fabric structure comprising at least one discrete layer of fibers sufficient to provide liquid barrier, said at least one layer being bounded on each side thereof by at least one discrete layer of coarse synthetic polymeric continuous filaments.

2. The coverstock of claim 1 wherein said at least one discrete layer of fibers sufficient to provide liquid barrier comprises fibers selected from the group consisting of synthetic polymeric continuous filaments, discontinuous synthetic polymeric fibers, and mixtures thereof.

3. The coverstock of claim 1 wherein said liquid transport region further comprises a surfactant to promote liquid strikethrough in the region.

4. The coverstock of claim 1 folded so that said liquid barrier region is comprised of a containment structure that bounds said liquid transport region on at least two sides.

5. The coverstock of claim 4 wherein said containment structure comprises barrier leg cuffs.

6. The coverstock of claim 4 wherein said containment structure comprises a waistband.

7. The coverstock of claim 1 comprising a spunbond-meltblown-spunbond bonded trilaminate structure having a continuous meltblown layer disposed between the spunbond layers and wherein said liquid transport region of said topsheet further comprises a surfactant to promote liquid strikethrough in said region.

8. The coverstock of claim 1 comprising a spunbond-meltblown-spunbond bonded trilaminate structure in which the meltblown layer is discontinuous across the structure, wherein said liquid barrier region is characterized by the presence of an intermediate meltblown layer and said liquid transport region is characterized by the absence of an intermediate meltblown layer.

9. The coverstock of claim 8 wherein said liquid transport region further comprises a surfactant to promote liquid strikethrough in the region.

10. The coverstock of claim 1 comprising a spunbond-meltblown-spunbond bonded trilaminate structure in which the meltblown layer is continuous across the structure, wherein said liquid barrier region is characterized by the presence of relatively fine meltblown barrier fibers and said liquid transport region is characterized by the presence of relatively coarse meltblown fibers to promote strikethrough.

11. The coverstock of claim 1 wherein said liquid barrier region is pervious to air, whereby said fabric is breathable.

12. A disposable absorbent article comprising a topsheet, a liquid impervious back sheet, and an absorbent core disposed therebetween, said topsheet comprising a nonwoven composite bonded fabric structure having a liquid transport region for strikethrough of liquid through the surface thereof bounded on at least one side thereof by a liquid barrier region, said liquid barrier region of said nonwoven composite bonded fabric structure comprising at least one discrete first layer of fibers sufficient to provide liquid barrier, said at least one first layer being bounded on at least the side thereof opposite said absorbent core by at least one discrete second layer of synthetic polymeric continuous filaments, and wherein said liquid transport region is comprised of said at least one discrete second layer of synthetic polymeric continuous filaments.

13. The disposable absorbent article of claim 12 wherein said at least one discrete first layer of said topsheet is comprised of fibers are selected from the group consisting of synthetic polymeric continuous filaments, discontinuous synthetic polymeric fibers, and mixtures thereof.

14. The disposable absorbent article of claim 12 wherein said liquid barrier region of said topsheet comprises synthetic polymeric continuous filaments of denier less than 1.

15. The disposable absorbent article of claim 12 wherein said liquid barrier region of said topsheet comprises substantially discontinuous meltblown fibers having a diameter of from about 2 to 15 microns.

16. The disposable absorbent article of claim 12 wherein said topsheet comprises a spunbond-meltblown-spunbond bonded trilaminate structure having a continuous meltblown layer disposed between said spunbond layers and wherein said liquid transport region of said topsheet further comprises a surfactant to promote liquid strikethrough in said region.

17. The disposable absorbent article of claim 16 wherein said surfactant is applied as a continuous stripe along the length of the topsheet.

18. The disposable absorbent article of claim 17 wherein said topsheet comprises a spunbond-meltblown-spunbond bonded trilaminate structure in which the meltblown layer is discontinuous across the web, wherein said liquid barrier region is characterized by the presence of an intermediate meltblown layer, and wherein said liquid transport region is characterized by the absence of an intermediate meltblown layer.

19. The disposable absorbent article of claim 12 wherein said liquid transport region of said topsheet further comprises a surfactant to promote liquid strikethrough in the region.

* * * * *

UNITED STATES PATENT AND TRADEMARK OFFICE
CERTIFICATE OF CORRECTION

PATENT NO. : 6,049,024
DATED : April 11, 2000
INVENTOR(S) : Thomas et al.

It is certified that error appears in the above-identified patent and that said Letters Patent is hereby corrected as shown below:

Column 15, in Table IV, first column, line 4, "290 ml" should read --200 ml--.

Signed and Sealed this

Twenty-fourth Day of April, 2001

Attest:

NICHOLAS P. GODICI

Attesting Officer

Acting Director of the United States Patent and Trademark Office